(12) United States Patent
Robinson

(10) Patent No.: US 8,808,307 B2
(45) Date of Patent: Aug. 19, 2014

(54) DRIVER FOR A SURGICAL DEVICE

(75) Inventor: Daniel Rae Robinson, Marquette, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 0 days.

(21) Appl. No.: 13/272,931

(22) Filed: Oct. 13, 2011

(65) Prior Publication Data

US 2012/0123431 A1 May 17, 2012

Related U.S. Application Data

(60) Provisional application No. 61/392,829, filed on Oct. 13, 2010.

(51) Int. Cl.
*A61B 17/58* (2006.01)

(52) U.S. Cl.
USPC .............................. 606/104; 606/99

(58) Field of Classification Search
USPC ............ 606/104, 86 A, 86 B, 86 R, 302, 305, 606/319; 411/407–408
See application file for complete search history.

(56) References Cited

U.S. PATENT DOCUMENTS

| | | |
|---|---|---|
| 2,317,319 A | 4/1943 | West |
| 2,404,427 A | 7/1946 | Bloomfield |
| 2,634,641 A | 4/1953 | Hodges |
| 2,737,988 A | 3/1956 | Gearhart et al. |
| 3,150,698 A | 9/1964 | Neil |
| 3,409,058 A | 11/1968 | La Pointe |
| 4,552,044 A | 11/1985 | Corona et al. |
| 4,813,808 A | 3/1989 | Gehrke |
| 4,924,736 A | 5/1990 | Bonner |
| 5,007,666 A | 4/1991 | Kyfes |
| 5,025,688 A | 6/1991 | Davis |
| 5,782,918 A | 7/1998 | Klardie et al. |
| 6,220,122 B1 | 4/2001 | Forsell et al. |
| 6,361,535 B2 | 3/2002 | Jackson |
| 6,382,977 B1 | 5/2002 | Kumar |
| 6,497,166 B1 | 12/2002 | Fleckenstein |
| 6,726,689 B2 | 4/2004 | Jackson |
| 6,786,903 B2 | 9/2004 | Lin |
| 6,904,836 B1 | 6/2005 | Andrei |
| 7,249,544 B2 | 7/2007 | Totsu |
| 7,338,286 B2 | 3/2008 | Porter et al. |
| 7,757,590 B2 | 7/2010 | Swartz |
| 7,862,588 B2 | 1/2011 | Abdou |
| 7,909,834 B2 | 3/2011 | Selover |
| 8,002,806 B2 | 8/2011 | Justis |

(Continued)

*Primary Examiner* — Todd Manahan
*Assistant Examiner* — Jessica Weiss
(74) *Attorney, Agent, or Firm* — Fitch, Even, Tabin & Flannery LLP

(57) ABSTRACT

A tool for holding or driving an implant member having a recess is provided including an elongate tool shaft having a distal head portion for being received in the recess and a securing mechanism that keeps the head portion in the drive recess and which is disposed proximally up along the tool shaft from the distal head portion. In one form, the securing mechanism includes a plurality of resilient leg member having distal end locking portions. In another form, a drive system includes a drive tool and a driven member. The drive tool has a generally annular flange portion that is radially larger than the drive head portion. The driven member has a generally annular securing portion for receiving the flange portion in releasably locked engagement so that the circumferential extent of the locking engagement is maximized relative to the smaller radial size of the drive head portion.

17 Claims, 19 Drawing Sheets

(56) References Cited

U.S. PATENT DOCUMENTS

| | | |
|---|---|---|
| 8,298,274 B2 | 10/2012 | Barker, Jr. et al. |
| 2005/0216015 A1 | 9/2005 | Kreidler |
| 2007/0093831 A1 | 4/2007 | Abdelgany et al. |
| 2008/0045955 A1* | 2/2008 | Berrevoets et al. ............. 606/61 |
| 2008/0154277 A1* | 6/2008 | Machalk et al. ................ 606/99 |
| 2010/0222827 A1 | 9/2010 | Griffiths et al. |
| 2012/0253397 A1 | 10/2012 | Kraus |

* cited by examiner

FIGURE 12
FIGURE 13
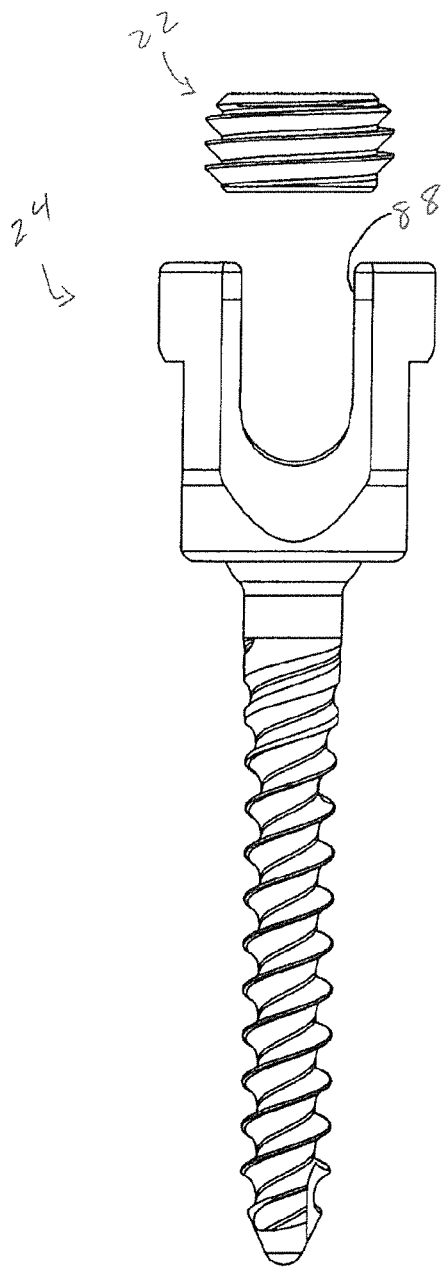
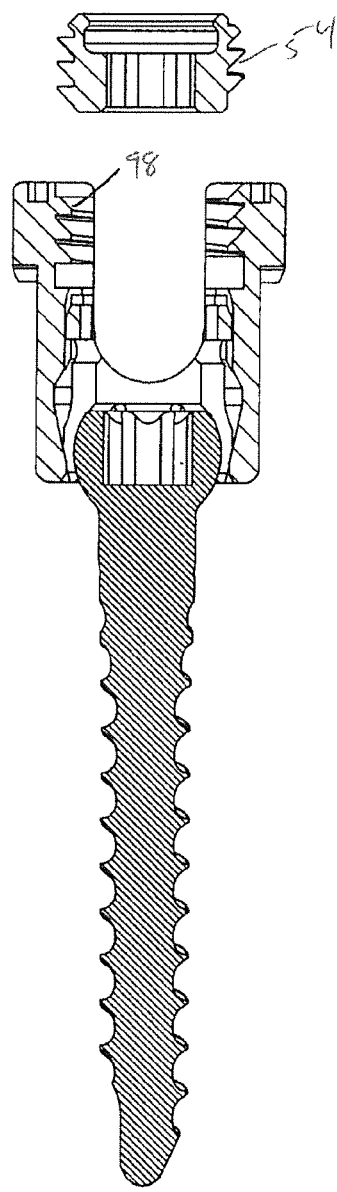

DRIVER FOR A SURGICAL DEVICE

CROSS-REFERENCE TO RELATED APPLICATIONS

This application claims the benefit of and priority to U.S. Provisional Application No. 61/392,829, filed 13 Oct. 2010.

FIELD OF THE INVENTION

The invention relates to a driver for surgical devices and, more particularly, to a drive tool for a locking device of a pedicle screw assembly.

BACKGROUND OF THE INVENTION

Typical driver tools have a drive head configured to mate with a drive recess of a threaded fastener to be driven by the tool. This is true with common hardware such as screw drivers and screws, as well as with hardware used in surgical devices such as with threaded locking caps for pedicle screw assemblies. However, in surgical operations, it is especially important that the driven member not be dropped on the floor or other area outside the sterile field, or otherwise lost in a body cavity at the surgical site.

Accordingly, there is a need for a driver that is able to securely hold a driven member as it is being driven, particularly one used for surgical devices.

SUMMARY OF THE INVENTION

In accordance with one aspect, a tool for driving and/or holding an implant member is provided with the tool including an elongate shaft having a portion that has both a distal head portion such as a drive head portion and a securing mechanism or portion disposed back up along the shaft from the distal head portion. The implant member can be various implants such as a threaded or non-threaded driven member, or a bone plate. In one form, where the implant member is a driven implant member, the drive portion can be provided at both ends of the tool shaft or at only one end thereof. In a preferred form, the distal drive head portion is provided with a radial size that is smaller than that of the corresponding radial size of the securing mechanism. In this manner, the circumferential extent of the locking engagement between the driver tool securing mechanism and the driven member is maximized relative to the radial size of the drive head portion.

In one form, the securing mechanism can comprise a plurality of resilient leg members that extend axially along the tool shaft and generally about the distal drive head portion thereof which projects beyond the ends of the resilient leg members. The leg members can have distal end locking portions that cooperate with structure of the driven member so that with the drive head portion of the tool shaft received in the corresponding drive recess of the driven member, the leg member locking portions will be secured to the driven member structure so that the driven member is positively held to the tool shaft against falling off therefrom.

In another aspect, the invention relates to a drive system which includes both the drive tool and the driven member. The driven member has a securing or locking structure or portion and a drive structure or portion sized for receiving the corresponding structures or portions of the drive tool. In one form, the driven member has a through bore including an upper, larger securing portion and a lower, smaller drive recess portion that correspond with the drive tool upper securing portion and distal drive head portion, respectively. In a preferred form, the upper securing portion of the through bore has an upper, inclined lead-in guide surface, and an undercut oppositely inclined locking surface therebelow. The drive tool has a plurality of resilient arm members each with a locking portion at the distal end thereof with the locking portions having corresponding oppositely inclined cam and locking surfaces that cooperate with the inclined guide surface and inclined locking surface of the driven member bore for camming the locking portions of the resilient arm members to be snap-fit into the upper securing portion of the driven member through bore. The smaller, lower portion of the through bore is configured to correspond to that of the distal drive head portion of the tool, such as a hexagonal cross-sectional configuration, so that the tool drive head portion is non-rotatably received therein. In a preferred form, the driven member has external threads for being received in an internally threaded surgical device when the driven member is held by the tool and turned thereby to be threaded to the device.

In an alternative form, the driven member has an external groove into which the locking portions are snap-fit by radially outward deflection of the resilient arms for connecting the driven member thereto before resiliently snapping back into the groove. In this form, the circumferential extent of the locking engagement between the drive tool securing mechanism is further maximized relative to the radial size of the drive head portion.

As indicated above, the inclined cam and locking surfaces of the tool arm members cooperate with the inclined surfaces of the driven member for securing the driven member to the tool, as by a snap-fit connection therebetween. More particularly, the lower cam surfaces of the locking portions of the tool resilient arm members are inclined relative to the axis of the tool shaft so that when the tool shaft is advanced linearly toward the driven member to insert the distal drive head portion thereof into the through bore, the lower cam surfaces of the arm members will engage the lead-in inclined guide surface of the driven member so that the resilient arm members are resiliently deflected radially inward toward each other. Continued insertion of the tool shaft into the driven member through bore will cause the upper ends of the lower cam surfaces to clear the lower ends of the guide surface until they reach the upper end of the lower, inclined locking surface of the driven member. With continued tool shaft insertion, the resilient arm members will resiliently shift radially outward so that the upper locking surfaces thereof are resiliently engaged tightly against the inclined locking surface of the driven member so as to be in axial interference therewith. With the drive head portion of the tool fully received in the lower drive portion of the driven member through bore, the locking surfaces of the tool and driven member will be in interfering engagement with one another such that the driven member is securely and positively held by the tool against falling off therefrom. Should the surgeon desire to remove the driven member from the tool, they will need to exert a separation force between the tool and the driven member to pull them away from one another which will cause the inclined locking surfaces of the tool and driven member to cam against one another until they are in clearance relative to each other to allow the driven member to be pulled off the tool.

BRIEF DESCRIPTION OF THE DRAWINGS

FIG. 12 is an elevational view of the pedicle screw assembly of FIG. 11 showing the outer coupling member, inner securing member, and bone screw in an assembled configuration with a threaded locking cap member shown in position to be threaded into the coupling member;

FIG. 13 is a sectional view of the pedicle screw assembly of FIG. 12 showing the cooperating threads of the locking cap member and the coupling member;

DETAILED DESCRIPTION OF THE PREFERRED EMBODIMENTS

Figure 1:
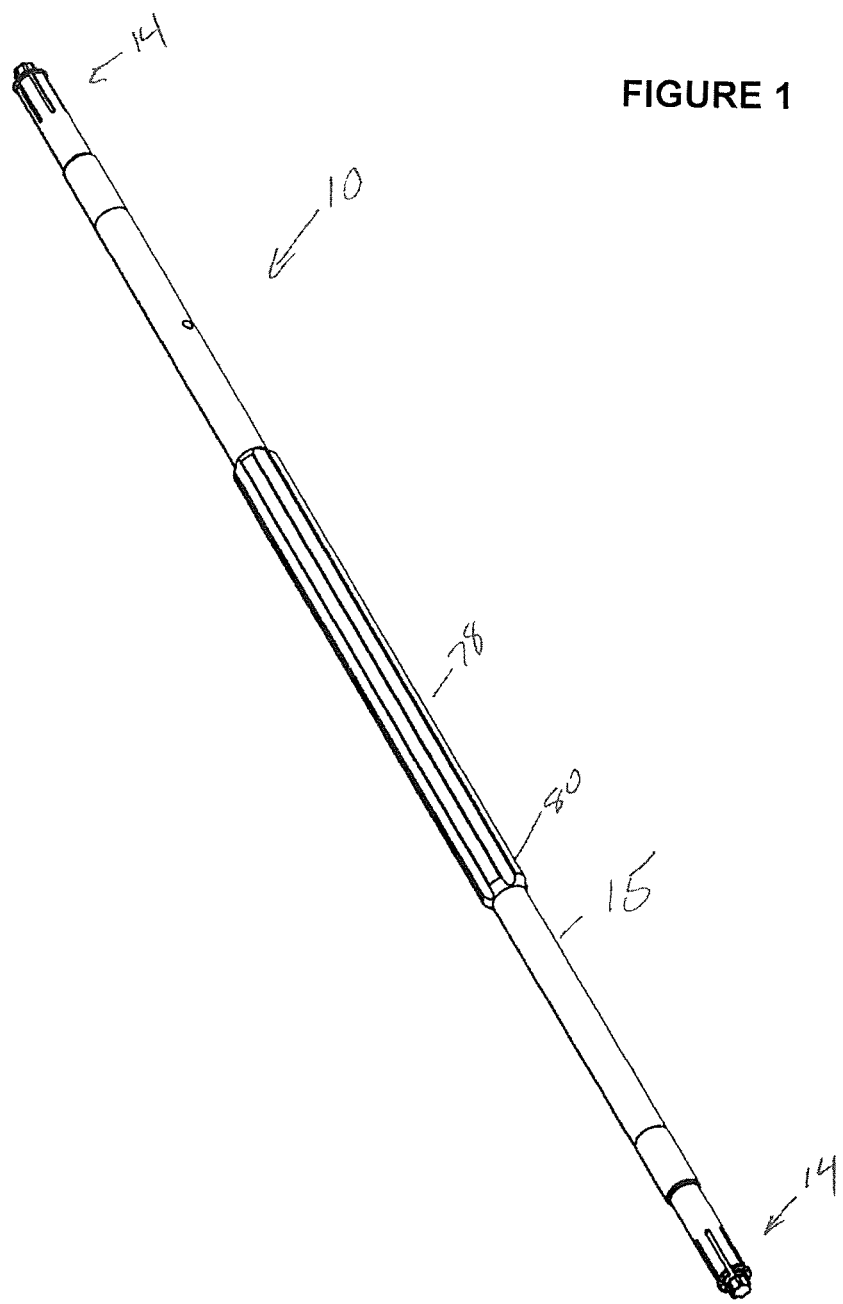
FIG. 1 is a perspective view of a drive tool having identical drive portions at either end thereof for driving a driven member with either end of the tool in accordance with the present invention.
Figure 1A:
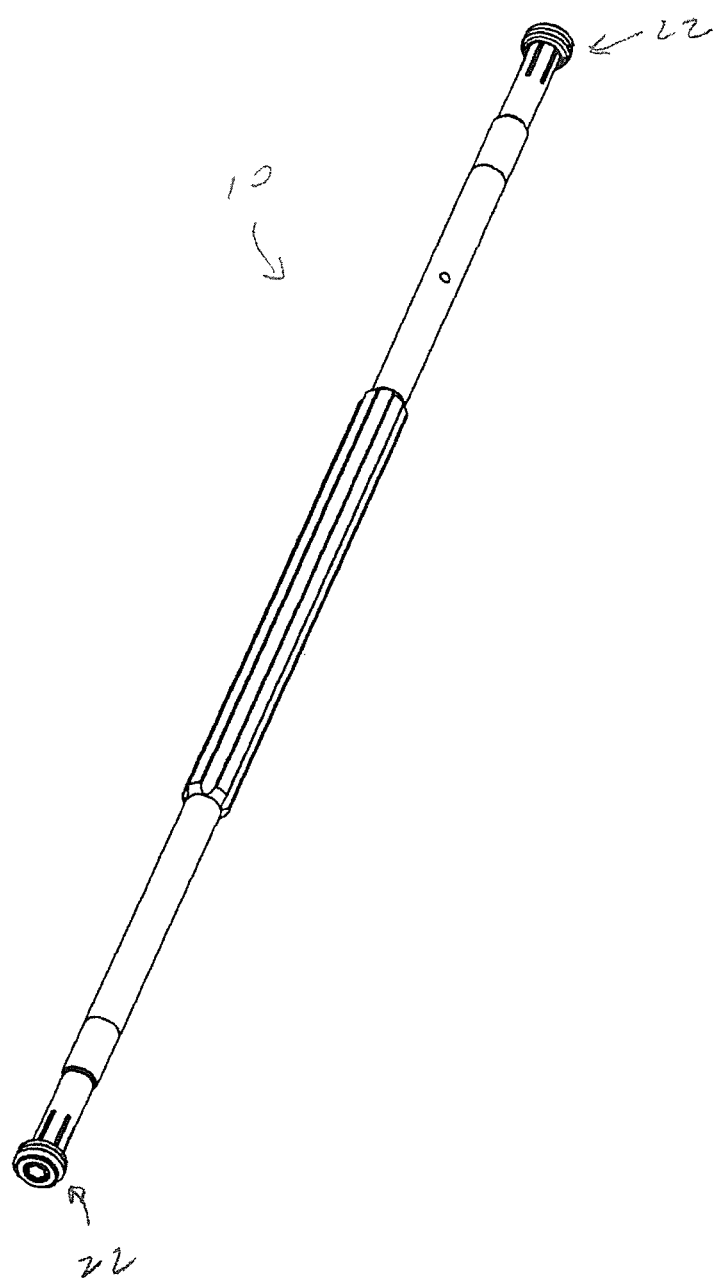
FIG. 1A is a perspective view showing driven members releasably connected to the drive tool of FIG. 1 at either end thereof.
Figure 2:
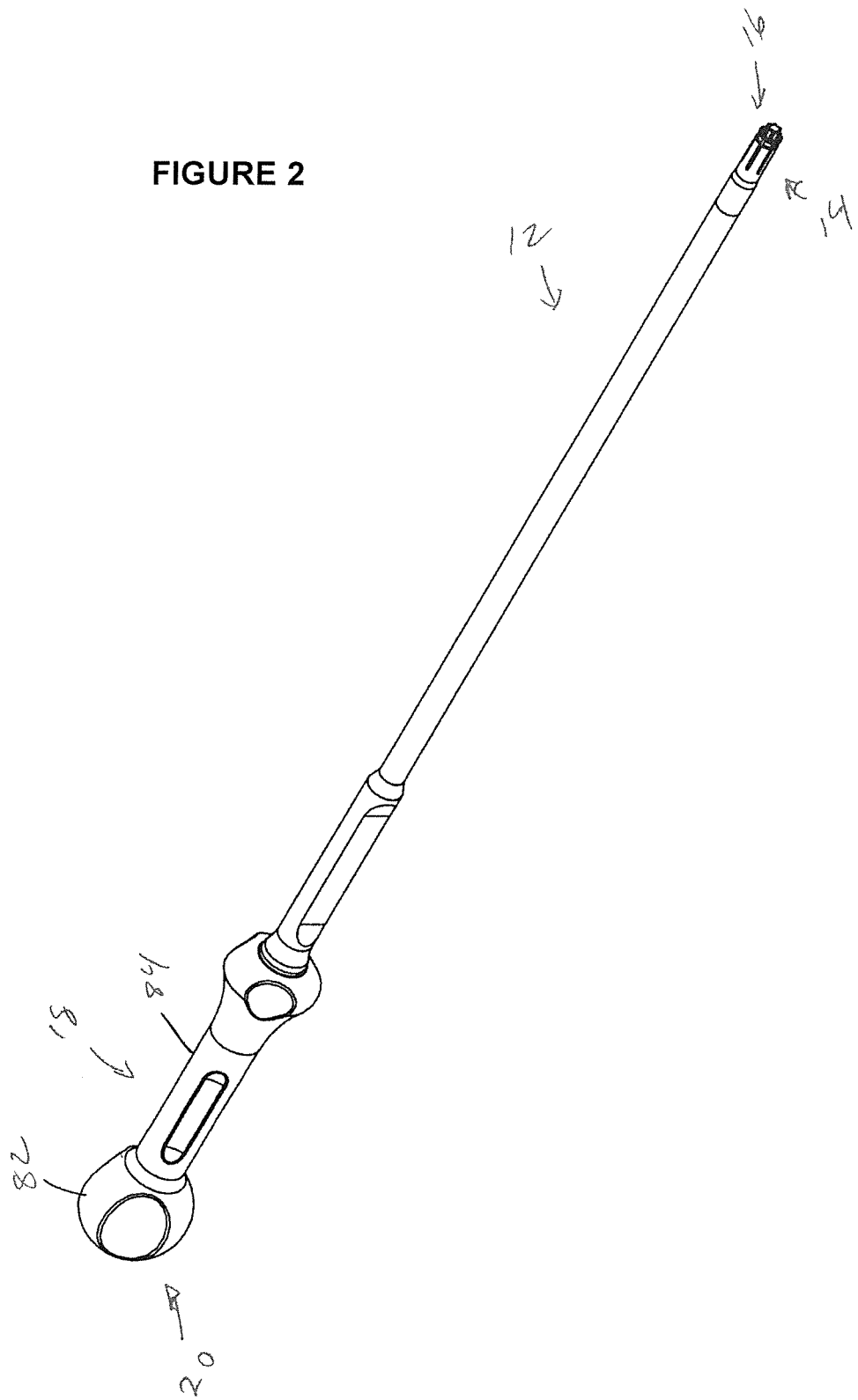
FIG. 2 is a perspective view of an alternative drive tool having a drive portion at only end of the tool for driving a driven member at the tool drive end.

In FIGS. 1 and 2, two drive tools 10 and 12 are illustrated with the tool 10 of FIG. 1 having two identical drive portions 14 at opposite ends of the tool shaft 15 whereas tool 12 has a single drive portion 14 at its distal end 16 and is provided with a gripping handle 18 at its proximal end 20. As will be described, the drive portion 14 is configured to both non-rotatably engage a driven member 22 such as in the form of an externally threaded locking cap device or member as shown in FIG. 3 as well as to securely hold it to the tool so as not to fall off therefrom during threading of the locking cap member 22 to, for example, pedicle screw assembly 24 (see FIGS. 11-14).

Figure 3:
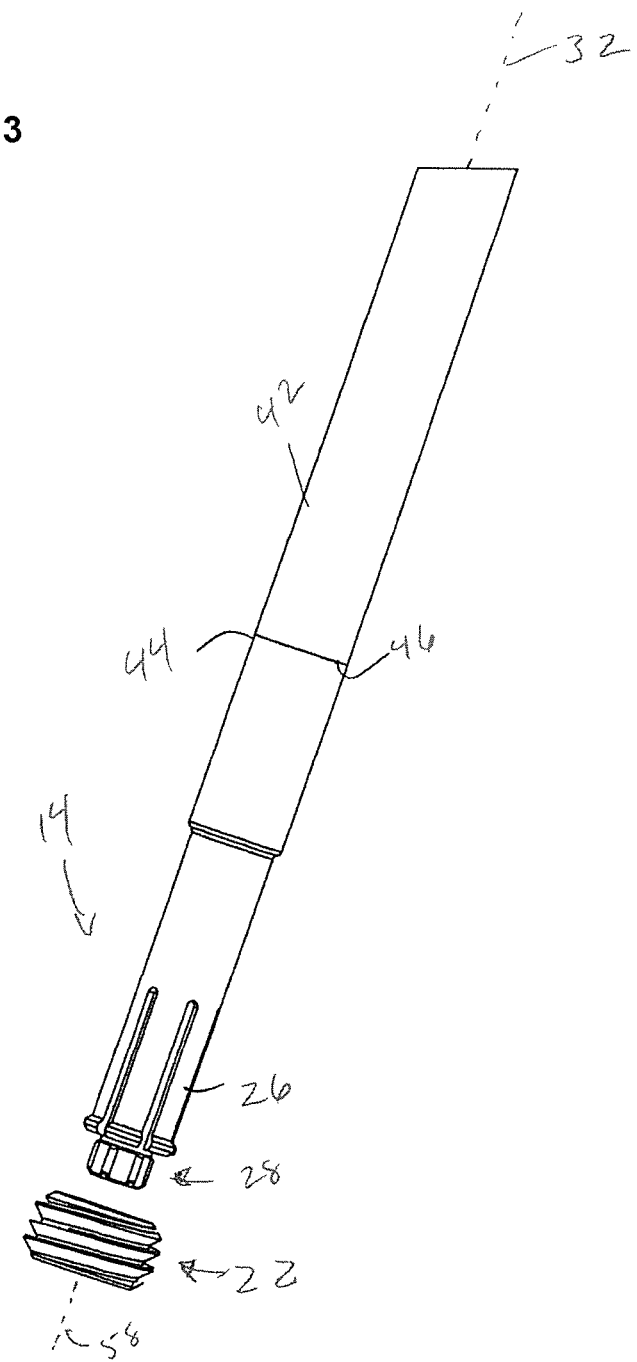
FIG. 3 is an elevational view of the tool drive portion showing resilient locking arms and a drive head portion projecting beyond the arms, and an externally threaded driven member in the form of a threaded cap locking member for a pedicle screw assembly for being rotatably driven by the drive tool.
Figure 4:
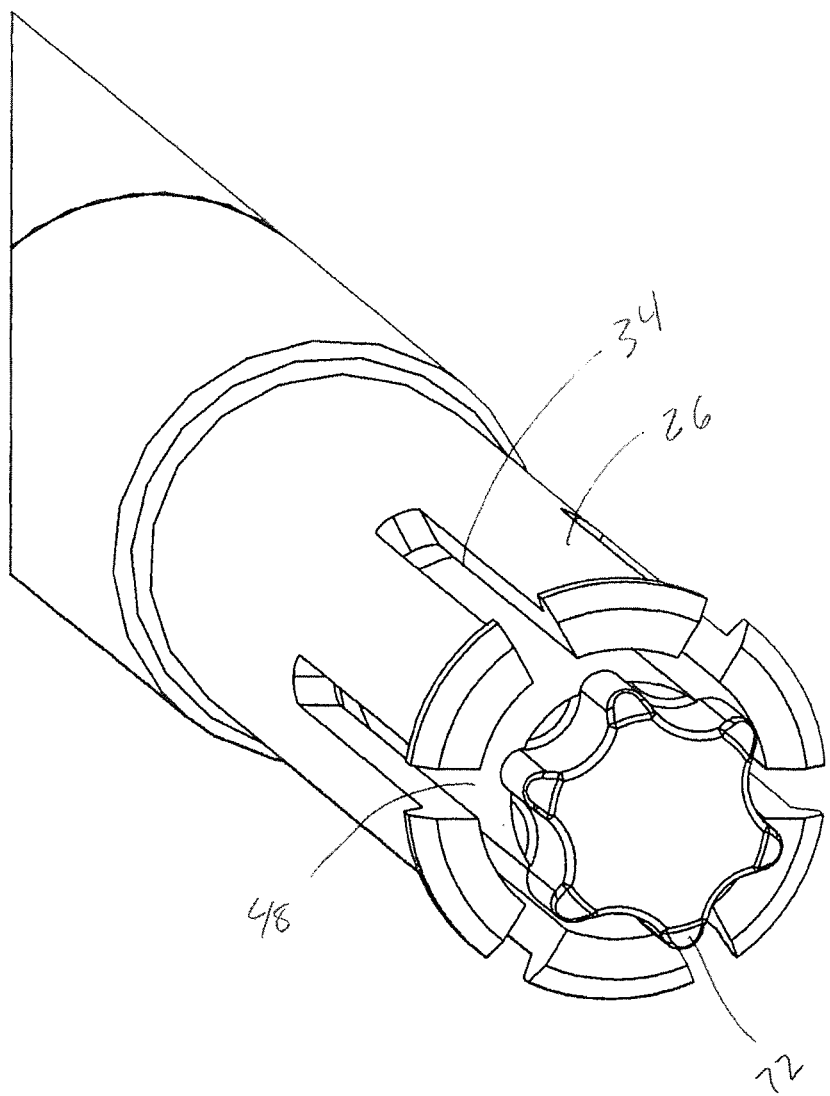
FIG. 4 is a enlarged perspective view of the tool drive portion showing elongate slots between the resilient locking arm members, and arcuate drive lobes of the drive head portion to provide the head portion with a hexagonal configuration.
Figure 5:
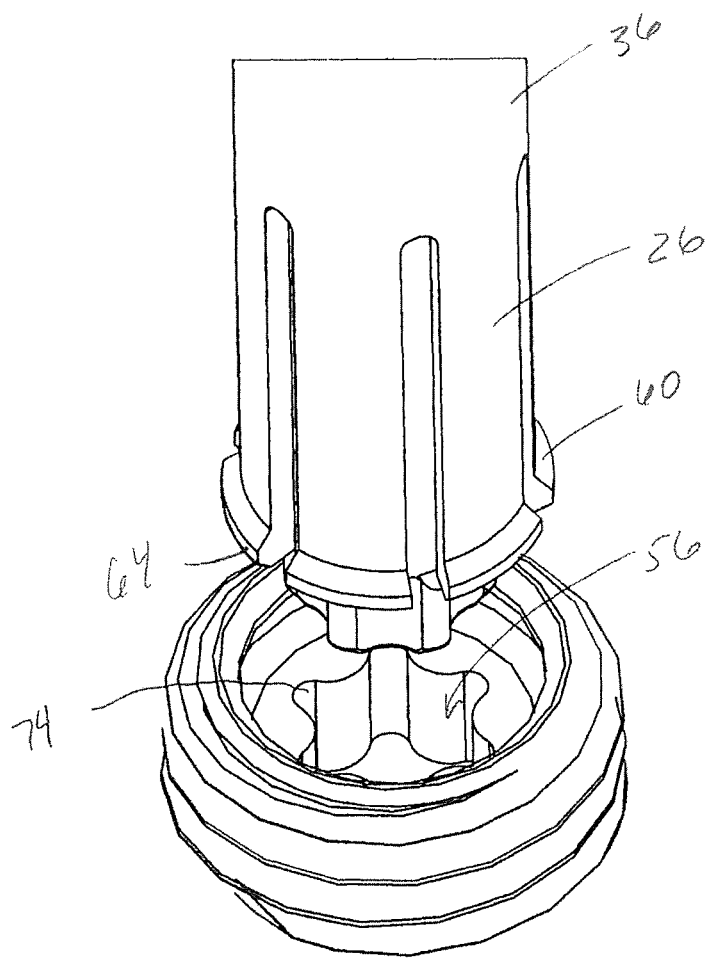
FIG. 5 is a perspective view of the tool drive portion and the threaded locking cap member showing a through bore of the locking cap member having a lower drive recess portion thereof provided with corresponding hexagonal configuration to the drive head portion of the tool.
Figure 5A:
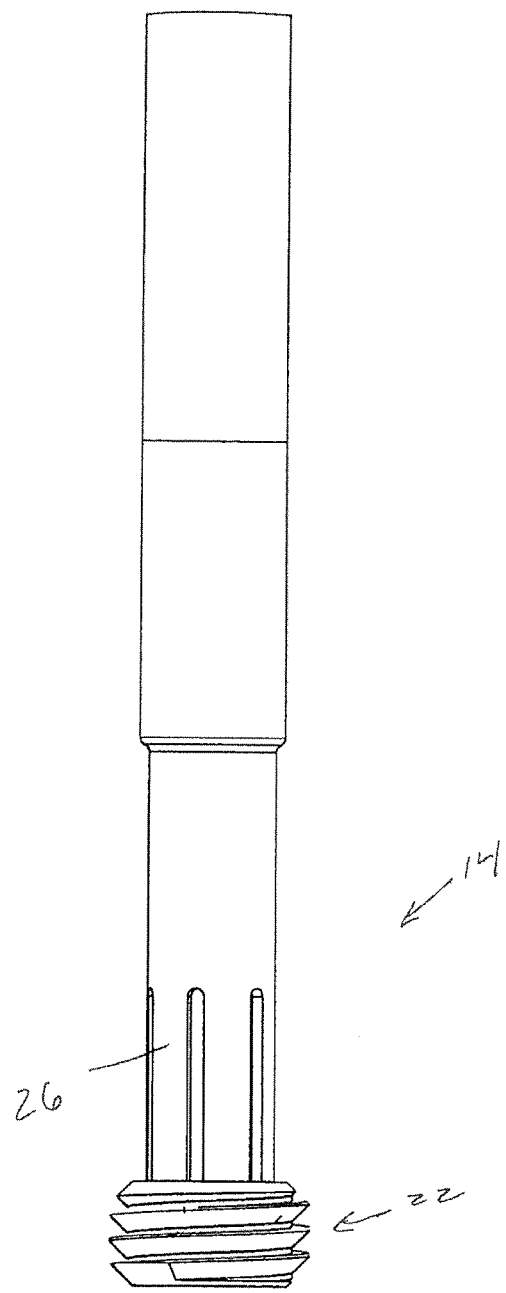
FIG. 5A is an elevational view showing the threaded locking cap member releasably connected to the tool drive portion.
Figure 8:
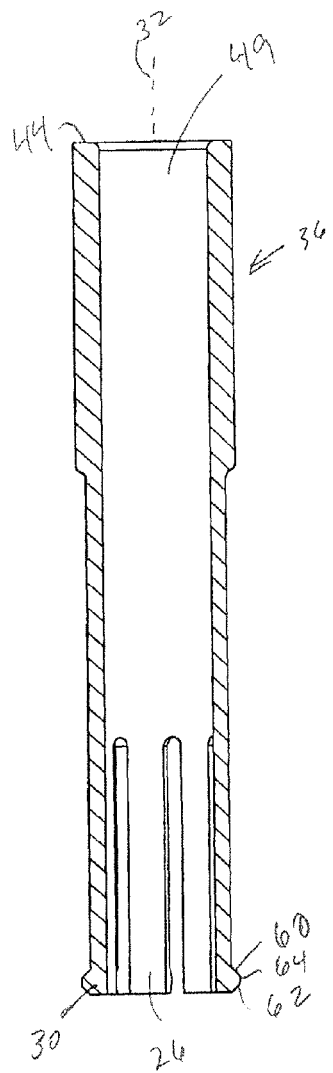
FIG. 8 is a sectional view of the sleeve member of FIGS. 6 and 7 showing upper, inclined locking surfaces and lower, inclined cam surfaces of the locking end portions of the arm members.
Figure 7:
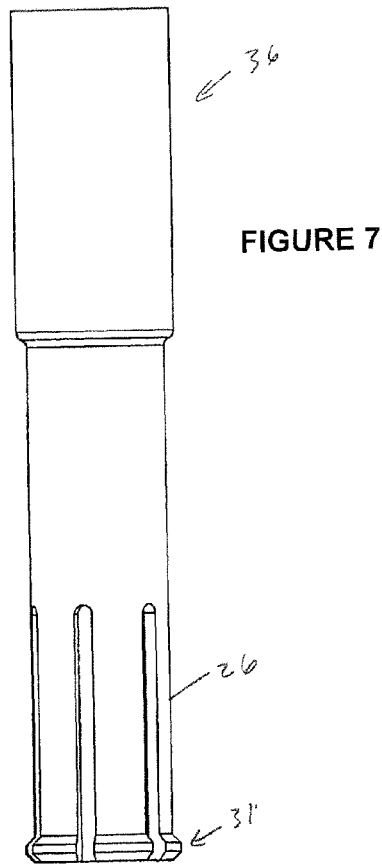
FIG. 7 is an elevational view of the sleeve member of FIG. 6 showing the wedge configuration of the locking end portions of the resilient arm members.

As can be seen in FIGS. 3-5, the drive portion 14 includes a plurality of resilient arm members 26 as well as distal drive head portion 28. The resilient arm members 26 are configured to securely engage and hold the locking cap member 22 to the tool shaft 15 while the drive head portion 28 transmits a rotational drive force to the locking cap member 22 as the shaft 15 is turned for threading the cap member 22 to internal threads of a surgical device, such as pedicle screw assembly 24, as previously mentioned. For this purpose, the resilient arm members 26 are each provided with a distal end locking portions 30 at their free ends, as can be seen best in FIGS. 7 and 8. The distal locking portions 30 are configured to cooperate with securing structure of the locking cap member 22 for securely and positively holding the cap member 22 to the tool shaft 15, as will be described more fully hereinafter. As can be seen, the resilient arm members 26 are recessed back up along tool shaft axis 32 from the bottom drive head portion 28 so that the drive head portion 28 extends down beyond the distal locking portions 30 of the resilient arm members 26.

Figure 6:
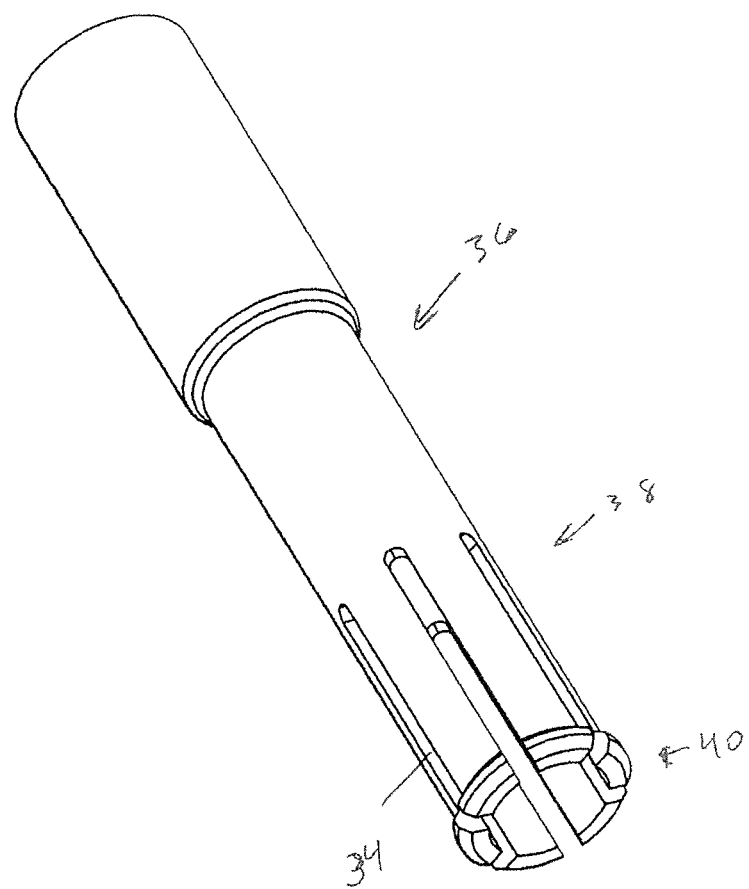
FIG. 6 is a perspective view of a sleeve member of the drive tool including the resilient arm members.

The resilient arm members 26 are formed by opened ended slots 34 that extend axially in sleeve member 36 at lower portion 38 thereof, as shown in FIG. 6. The slots 34 extend to the distal end 40 of the sleeve member 36 opening thereat so as to create separation between the resilient arm members 26, and particularly between the distal locking portions 30 at the sleeve distal end 40. The distal locking portions 30 taken together form a radially enlarged lower flange portion 31 having a generally annular configuration interrupted by the slots 34 at the distal end 40 of the sleeve member 36, as can be seen best in FIGS. 4 and 6. The resiliency of the arm members 26 can be controlled by varying the axial length and circumferential width of the slots 34, as well as by varying the radial thickness of the arm members 26 and the material from which the sleeve member 36 is formed. In practice, the axial length of the arm members 26 is approximately 0.480 inch, the circumferential width of the slots 34 is approximately 0.032 inch, and the material of the sleeve member 36 is titanium or stainless steel.

The resilient arm members extend down along the tool shaft 15 about axis 32 thereof when the sleeve member 36 is fixedly secured to main shaft 42 as by braze welding of the proximate end 44 of the sleeve member 36 to the lower shoulder 46 of the main shaft 42. In this regard, the main shaft 42 has a reduced lower shaft portion 48 that extends axially downwardly from the lower shoulder 46. The lower shaft portion 48 extends in through bore 49 of the sleeve member 36 when fixedly connected to the main shaft 42 and beyond the locking portions 30 at the end 40 thereof to the drive head portion 28 of the lower shaft portion 48. As such, the resilient arm members 26 are disposed about the lower shaft portion 48 and secure the locking cap member 22 to the shaft 15 generally above and about the drive area where drive head portion 28 engages in the locking cap member 22. As can be seen in FIG. 4, there is radial clearance between the resilient arm members 26 and the lower shaft portion 48 to allow the resilient arm members 26 to deflect radially inward toward the shaft portion 48 as the locking cap member 22 is secured thereto.

Figure 9:
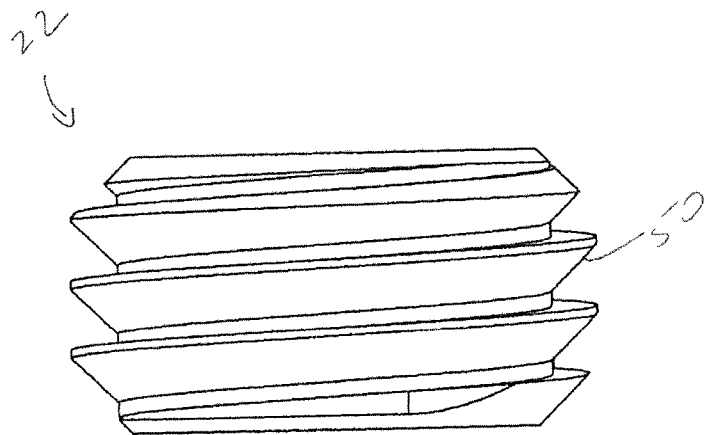
FIG. 9 is a elevational view of the externally threaded locking cap member.
Figure 10:
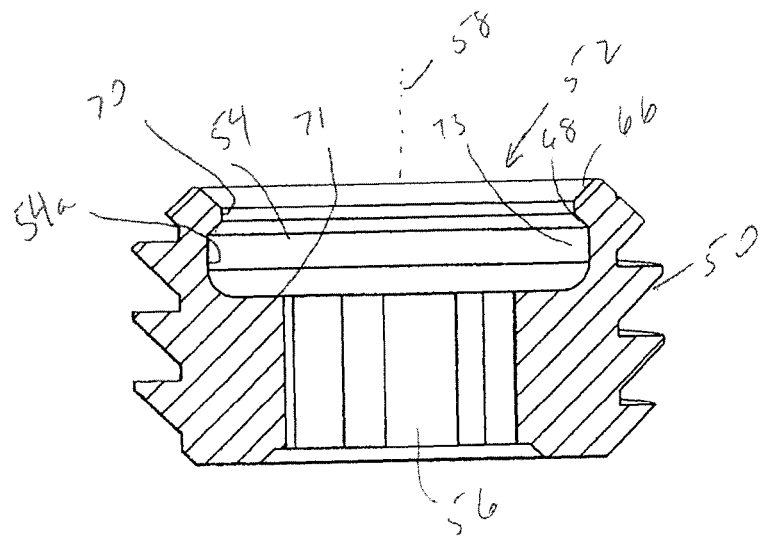
FIG. 10 is a sectional view of the locking cap member showing the through bore including a radially smaller, lower drive recess portion and radially larger, upper securing portion thereof.

The illustrated locking cap member 22 is in the form of a threaded nut such as of titanium material and has external threads 50 and a through bore 52, as shown in FIGS. 5, 9 and 10. Alternatively, the cap member 22 can be non-threaded and be configured to cooperate with, for example, a non-threaded component of the pedicle screw assembly 24 for being secured thereto. The through bore 52 has a radially larger upper, securing portion 54 including internal surfaces for cooperating with the resilient arm members 26, and a radially smaller, lower drive recess portion 56 including inner surfaces for cooperating with the drive head portion 28. As can be seen in FIG. 5, the interior surfaces of the through bore upper portion 54 have a generally annular configuration, while the interior surface of the through bore lower portion 56 can have a lobed, hexagonal configuration so as to receive the correspondingly configured drive head portion 28 in a mating fit therein.

Since the lower flange portion 31 formed by the locking portions 30 is radially larger than the radially smaller drive head portion 28, the circumferential extent or distance of the locking engagement between the locking portions 30 and the annular surfaces of the bore upper portion 54 is maximized relative to the radially smaller drive head portion 28. This arrangement provides for a reliable, secure and strong connection between the tool 10 and the locking cap member 22. In this regard, the diameter across generally diametrically opposite locking portions 30 can be approximately 0.270 inch, and the largest diameter across the drive head portion 28, such as across generally diametrically opposite lobe projections, can be approximately 0.180 inch. With these dimensions, the effective diameter across the locking portions 30 of flange 31 is 50% larger than the largest effective diameter of the drive head portion 28. In this context, the largest effective diameter of the lobed drive head portion 28 is the distance across the radially outwardmost points of opposite lobes of the drive head portion 28.

In addition, it should be noted that the drive head portion 28 and cooperating drive recess portion 56 are configured to have a non-rotatable mating fit with each other so that each has a corresponding cross-sectional shape that is other than circular, e.g., the lobed, hexagonal configuration shape described above. With the illustrated lobed, hexagonal, cross-sectional configuration, the drive head portion 28 and the drive recess portion 56 despite having a smaller diameter than the locking flange portion 31, provide a driving area of engagement between their mating surfaces that is great enough to enable a surgeon to readily and securely apply sufficient torque to the cap member 22 for rotatably driving it to be secured to the pedicle screw assembly 24.

To provide the secure connection between the tool shaft 15 and the locking cap member 22, surfaces of the distal locking portions 30 are provided that are inclined relative to the shaft axis 32 for cooperating with surfaces of the through bore upper securing portion 54 that are inclined with respect to the axis 58 of the locking cap member 22. Referencing FIGS. 7 and 8, the locking portions 30 each have an upper, inclined locking surface 60 that tapers away from the central, longitudinal shaft axis 32 as the surface 60 extends downwardly. The locking portions 30 each further include a lower inclined cam surface 62 that has a reverse incline relative to the upper locking surface 60 so that it tapers back toward the shaft axis 32 as the surface 62 extends downwardly to the end 40 of the sleeve member 36. Extending between the radially outer ends of the surfaces 60 and 62 is an axially extending intermediate surface 64 such that the surfaces 60-64 provide each of the locking portions 30 with a generally wedged shaped configuration.

Referencing FIG. 10, the annular interior surfaces of the through bore portion 54 of the locking cap member 22 include an upper, lead-in guide surface 66 that is inclined relative to the axis 58 so as to taper inwardly as it extends downwardly in the through bore 52 from a larger diameter at its upper end to a smaller diameter at its lower end. The through bore 52 further includes a lower locking surface 68 that is undercut so that it has a reverse incline relative to the upper guide surface 66 to taper from its smaller diameter upper end down to a larger diameter lower end at an incline from axis 58. Intermediate, axially extending surface 70 interconnects the lower end of the upper guide surface 66 and the upper end of the lower locking surface 68. The through bore upper portion 54 has a bottom surface 71, and the drive recess lower portion 56 is formed centrally in the bottom surface 71 to extend downwardly therefrom.

To secure the locking cap member 22 onto to the tool shaft 15, the drive head portion 28 is advanced into the through bore 52 bringing the lower cam surface 62 of the shaft 15 into engagement with the upper guide surface 66 of the locking cap member 22. Continuing to advance the drive head portion 28 axially into the bore 52 causes the resilient arm members 26 to be deflected radially inwardly due to the camming action between the engaged inclined surfaces 62 and 66, until the upper end of the cam surface 62 clears the lower end of the guide surface 66. At this point, continued insertion of the drive head portion 28 causes the corresponding axially extending intermediate surfaces 64 and 70 to engage each other until the upper end of the surface 64 clears the lower end of the surface 70. At this time, the resilient arm members will shift radially outward by resiliently snapping back toward their undeformed configuration so that the upper locking surface 60 is tightly and resiliently engaged with the lower locking surface 68 of the locking cap member 22, and the intermediate surface 64 is tightly and resiliently engaged with axially extending annular surface 54a extending about bore upper portion 54 and extending axially between the lower end of the lower locking surface 68 and the radially outer end of the bottom surface 71. The snap-fit of the resilient locking portions 30 in the bore upper portion 54 provides the surgeon tactile and audible feedback to indicated that the cap member 22 is releasably locked to the tool 10. With the lobe projections 72 of the drive head portion 28 aligned with the corresponding lobe recesses 74 of the lower drive recess portion 56 of the locking cap member through bore 52, the drive head portion 28 can be received with a mating fit in the correspondingly configured lower drive recess portion 56 with the locking surfaces 60 and 68 fully engaged with each other.

Figure 5B:
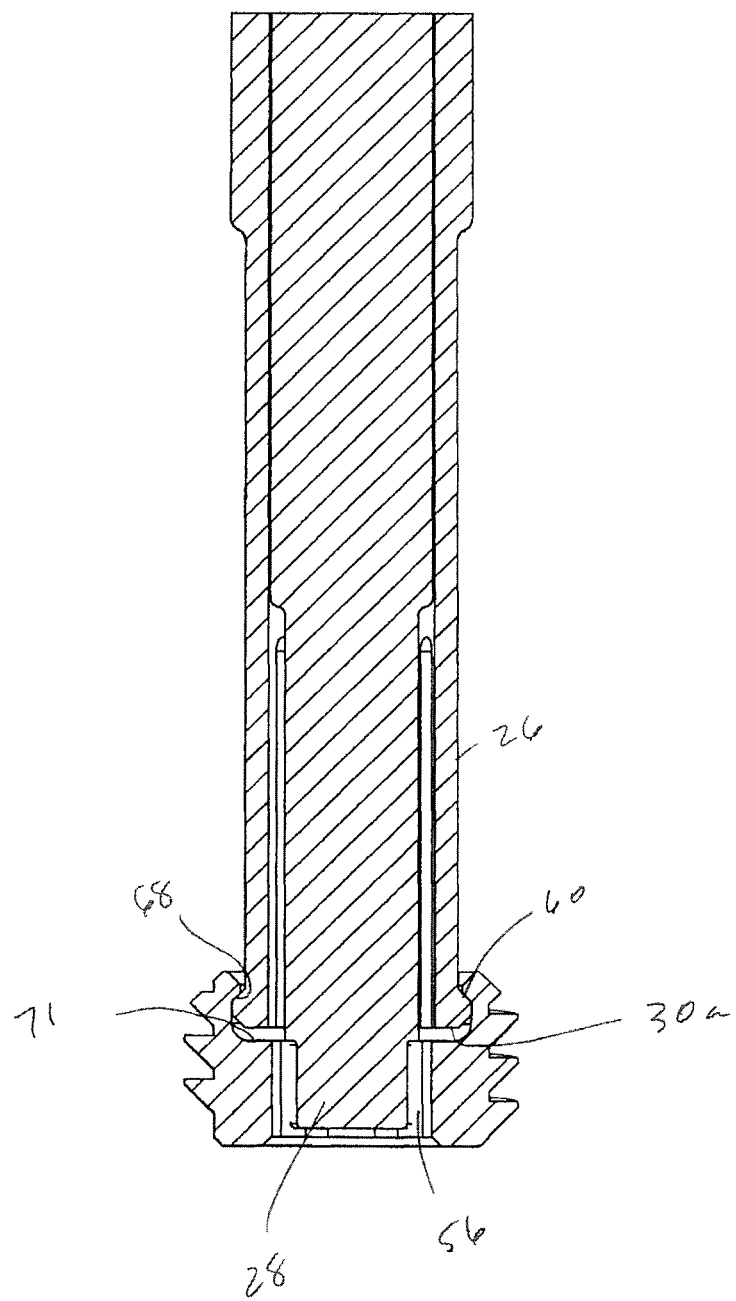
FIG. 5B is a sectional view showing locking end portions of the resilient locking arm members received in an elevated position in an undercut pocket in a through bore of the locking cap member.

In this configuration, the arm locking portions 30 are fully received in an undercut pocket 73 between the inclined locking surface 68 and the bottom surface 71 of the bore upper portion 54 with the locking surfaces 60 and intermediate surfaces 64 of the resilient arm members 26 tightly engaged against the respective locking surface 68 and annular surface 54a of the locking cap member through bore 52 due to the resilient configuration of the arm members 26. In this manner, the surfaces 60 and 64 will be resiliently biased into tight engagement with the respective surfaces 68 and 54a to provide a secure connection between the tool shaft 15 and the locking cap member 22 above and generally around the non-rotatable, driving engagement between the mating drive head portion 28 and the lower drive recess portion 56 of the cap member through bore 52, as shown in FIG. 5B.

Figure 5C:
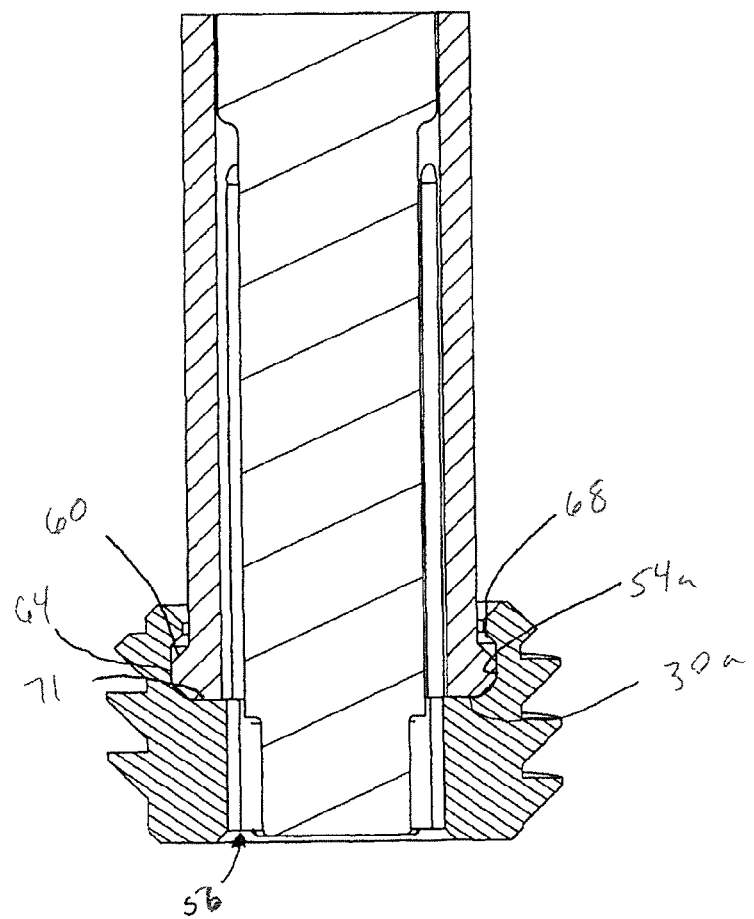
FIG. 5C is a section view similar to FIG. 5B showing the locking end portions received in a lowered position in the through bore pocket.

It can be seen that the undercut pocket 73 is axially longer than the arm locking portions 30 such that there is a small amount of axial play therebetween. FIG. 5C shows the locking projections 30 fully bottomed out in the through bore upper portion 54 so that bottom surfaces 30a of the locking projections 30 are engaged against the bottom surface 71 of the bore upper portion 54 with the surfaces 60 and 68 separated from each other. However, the surfaces 64 and 54a are still tightly and resiliently engaged with each other due to the resilient nature of the arm members 24 as discussed above, and the cap member 22 cannot fall off the tool shaft 15 since the locking surfaces 60 and 68 remain in axial interference with one another. Referencing FIGS. 5B and 5C, it can be seen that the drive head portion 28 and specifically the lobe projections 72 thereof extend axially beyond the bottom surfaces 30a of the arm locking projections 30 by a predetermined distance that generally corresponds with the axial length of the drive recess portion 58 and specifically the lobe recesses 74 thereof. In this manner, when the arm locking projections 30 are bottomed out in the through bore upper portion 54 via engagement of the respective surfaces 30a and 71 thereof, the lobe projections 72 will be in mating relation with the corresponding lobe recesses 74 for substantially the full axial extent of one another, as shown in FIG. 5C.

To remove the locking cap member 22, a separation force must be applied between the tool shaft 15 and cap member 22 as by pulling them apart from each other to cause the engaged, inclined locking surfaces 60 and 68 to cam against each other for deflecting the resilient arm members 26 sufficiently radially inward to allow them to be pulled out of the bore 52. This can be done after the locking cap member 22 is threaded to the pedicle screw assembly 24, or by the surgeon prior thereto if desired. In this regard, with the configuration of the tool 10 and cap member 22 herein, and particularly with respect to the identical inclination of the cooperating locking surface 60 and cam surface 62 of the resilient arm locking portions 30 albeit in reverse directions and the guide surface 66 and locking surface 68 of the cap bore surfaces from the tool shaft axis 32 and cap member axis 58, respectively, the pressure required to both connect and disconnect the tool 10 and the cap member 22 can be identical.

By way example, with the inclined surfaces 60 and 62 of the tool 10 and inclined surfaces 66 and 68 of the cap member 22 each having an angle of approximately 45° from the tool and cap member axes 32 and 58, respectively, the pressure required to both connect and disconnect the tool 10 and the cap member 22 has been found to be approximately 3 lbs. Advantageously, this allows the surgeon to know how much pressure they will need to use for both connecting the cap member 22 to the tool 10 and for disconnecting it from the tool 10. If desired the angles of the inclined surfaces could be made different from each other to require greater or less pressure to connect the cap member 22 to the tool 10 as compared to disconnecting it therefrom. It has further been found that the tool 10 herein provides a durable and robust lock with the cap member 22 as testing has shown a loss of less than 8 percent of the holding power over 5200 repetitions of connecting and disconnecting the cap member 22 to and from the tool 10. This is reflective of the lack of wear of the tool 10 over repeated uses, and particularly of the surfaces 60-64 of the resilient locking portions 30 which stands in stark contrast to prior surgical drive tools that employ a taper-type lock with the driven member which are prone to a much higher wear rate and thus a much shorter functioning life span.

Turning to more of the details, as previously discussed the tool 10 has a pair of drive portions 14 at either end thereof whereas the tool 12 only has the drive portion 14 at the distal end 16 thereof. The tool 10 provides the surgeon with the option of loading two locking cap members 22 onto the tool shaft 15 which may be beneficial where a spinal rod 76 extends through multiple pedicle screw assemblies 24 that need to be locked down with corresponding multiple locking cap members 22. In this instance, the shaft is provided with an intermediate gripping portion 78 for the surgeon to turn the shaft 15 for threading the locking cap members 22 securely held onto the drive portions 14 at either end thereof into the pedicle screw assemblies 24. The gripping portion 78 can be enlarged relative to the remainder of the shaft 15 and be provided with gripping features, such as axially extending knurled or raised rib portions 80 or the like to allow for enhanced gripping on the shaft gripping portion 78. Alternatively and as previously described, the tool 12 of FIG. 2 has a gripping handle 18 at the proximal end 20 of the shaft 15 to provide an area for the surgeon to grip for turning the shaft 15 with the locking cap member 22 secured thereto to thread it to the pedicle screw assembly 24. The handle 18 includes an enlarged knob end 82 and an elongate gripping surface 84 below the knob end 82 that tapers outwardly at the bottom thereof to provide an area for the handle 18 to be gripped by the surgeon.

Figure 11:
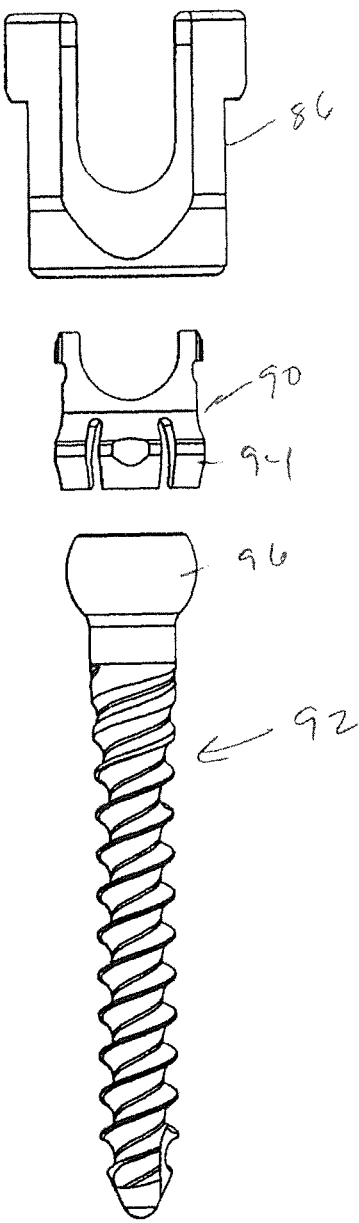
FIG. 11 is an elevational view of a pedicle screw assembly showing an outer coupling member for receiving a spinal rod extending transversely therethough, an inner securing member, and a bone screw.
Figure 14:
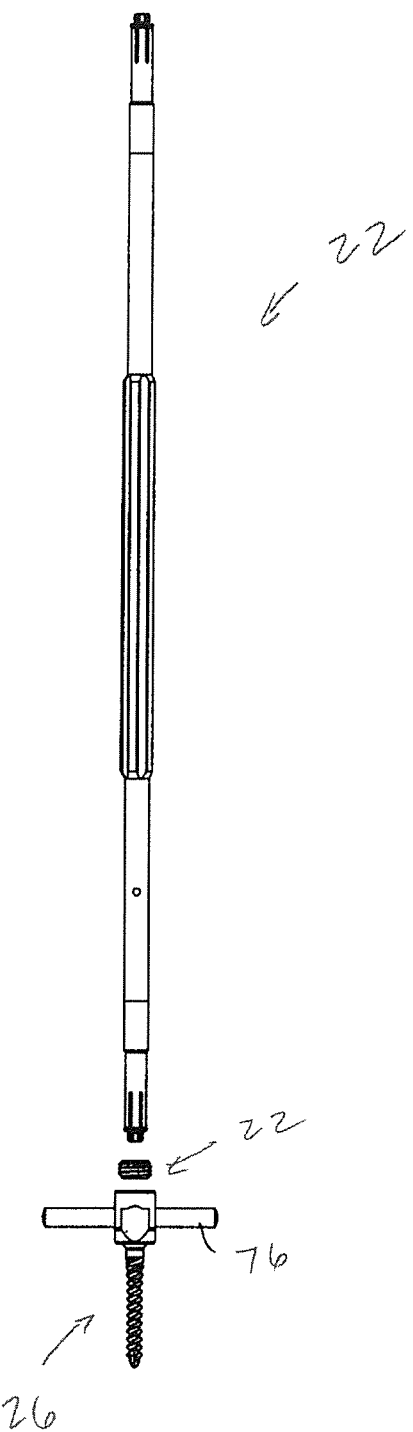
FIG. 14 is an elevational view of the drive tool of FIG. 1 in position to receive the locking cap member thereon for being threaded into the coupling member of the pedicle screw assembly to lock a spinal rod therein.

Referring next to FIGS. 11-14, the illustrated pedicle screw assembly 24 has an outer coupling member 86 having diametrically opposite upwardly opening slots to allow the spinal rod 76 to extend transversely therethrough. The pedicle screw assembly 24 further includes an inner locking sleeve member 90 for locking the multi-axial bone screw 92 in a specific angular orientation relative to the coupling member 86. As shown in FIG. 11, the inner locking member 90 has resilient locking arms 94 that are tightly clamped onto the bone screw head 96 as the locking sleeve 90 is advanced downwardly in the outer coupling member 86, or alternatively or additionally as the outer coupling member 86 is drawn upwardly relative to the inner locking sleeve 90. The outer coupling member 86 has upper interior threads 98 that are configured to threadingly engage the external threads 54 of the locking cap 22 for locking the spinal rod 76 in the pedicle screw assembly 24.

Figure 15:
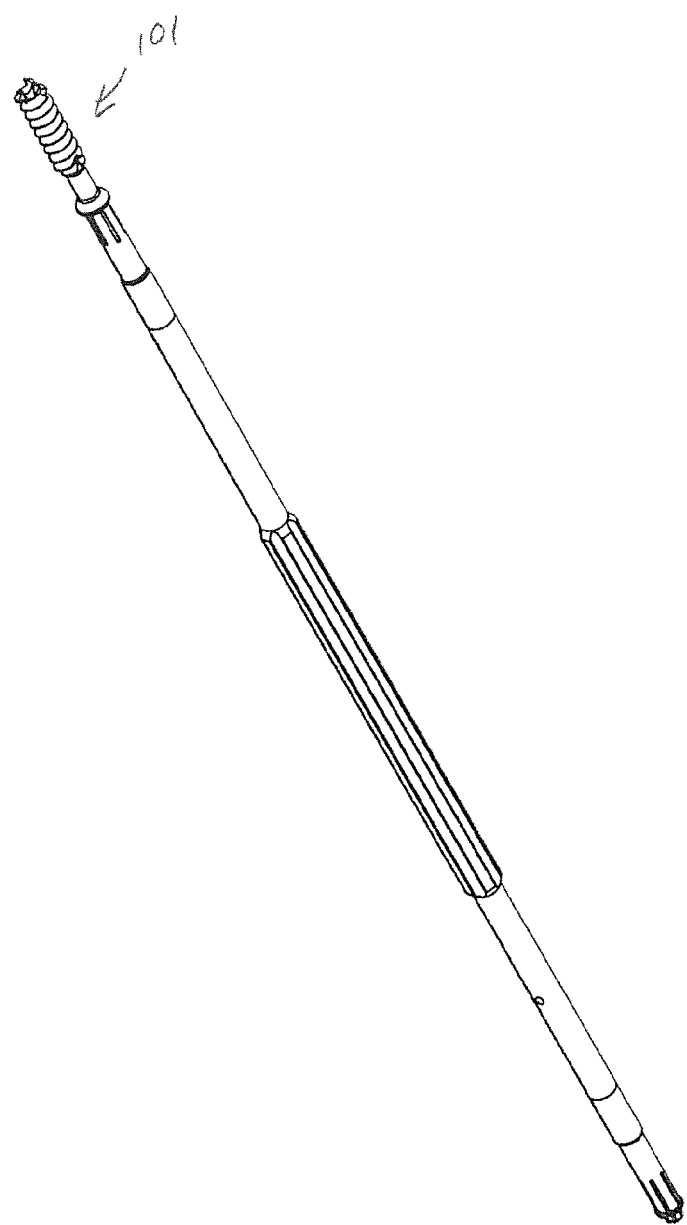
FIG. 15 is a perspective view of the drive tool of FIG. 1 having a different driven member in the form of a bone screw releasably connected thereto.
Figure 16:
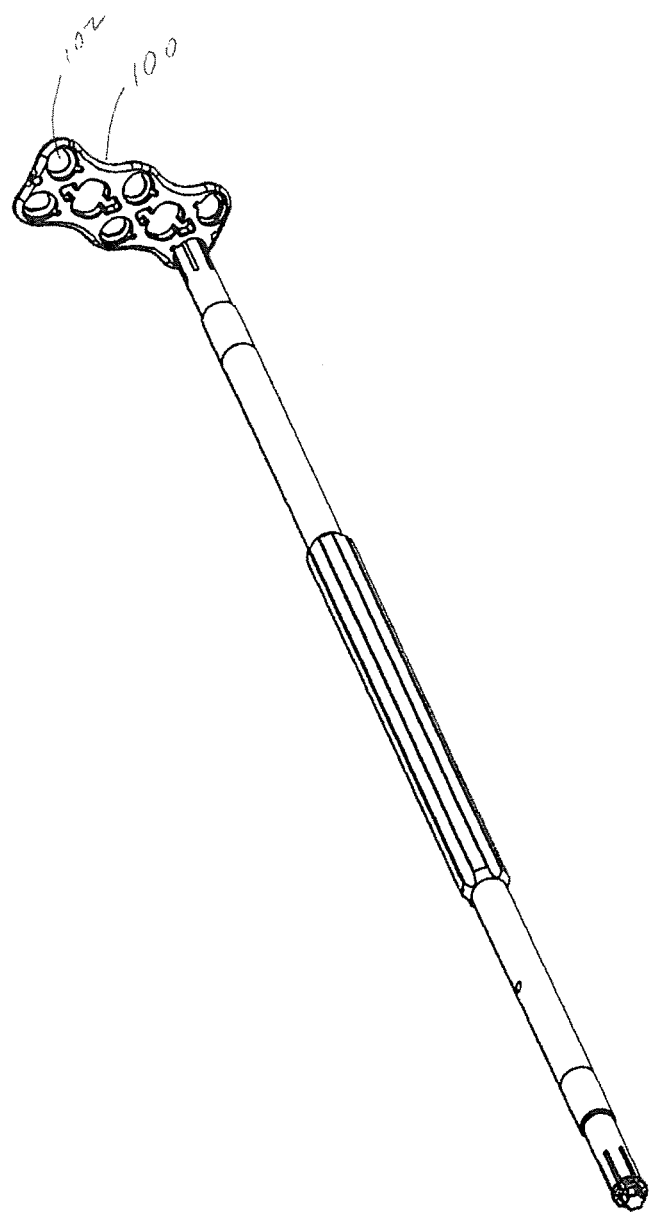
FIG. 16 is a perspective view showing the tool as a holding tool having a bone plate secured thereto.

Manifestly, other configurations and arrangements of pedicle screw assemblies can be utilized with a threaded member similar to locking cap member 22 that is threaded to the pedicle screw assembly with the driver tools disclosed herein. Further, the driver tools described herein can be used advantageously for holding and/or driving other implant members for different types of surgical devices such as for holding the illustrated bone plate 100 of FIG. 16. The driver tool 12 can be utilized to drive a threaded bone screw 101 (FIG. 15) or retainer therefor releasably connected thereto through the bores 102 of the bone plate 100 for the bone screws 101 and into the underlying bone. The bone screw bore is configured similar to the bore of locking cap member 22 for receiving the drive portion of the drive tool therein. Alternatively, where used as a holding tool for the bone plate 100, the bone plate bores 102 are configured similar to the bore of the locking cap member 22, but the head portion of the holding tool 12 and the portion of the bore in which the head portion is received need not be configured to have an engaged driving relation. As will be appreciated, the driver tool 12 herein is especially useful for driving relatively small driven members that require an applied driven torque and which are used in surgical procedures, such as a crimping member for a crimping device for surgical cables.

Figure 17:
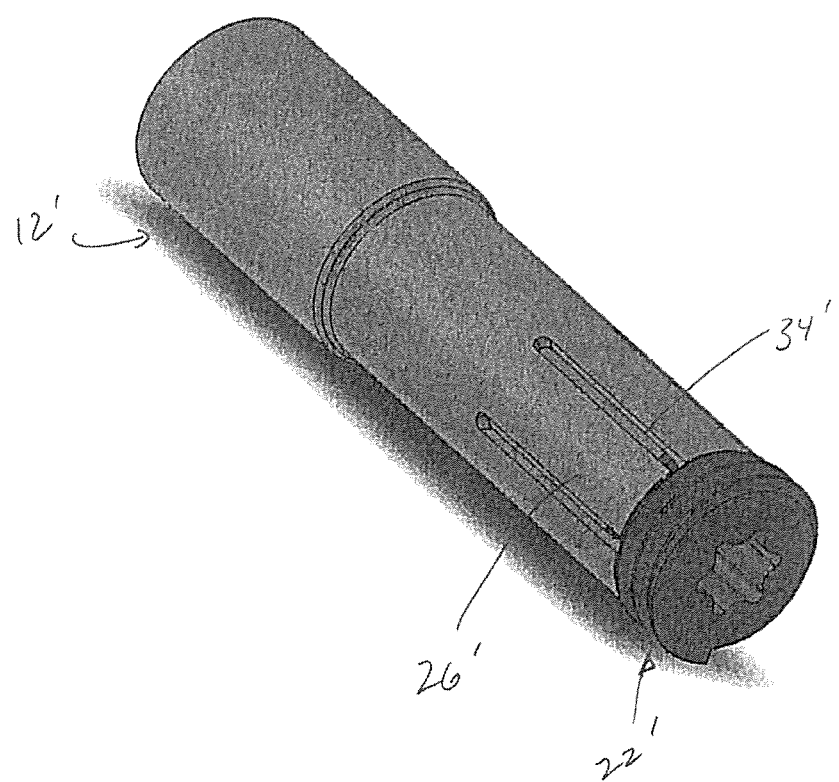
FIG. 17 is a perspective view of an alternative drive tool and driven member releasably connected thereto.
Figure 18:
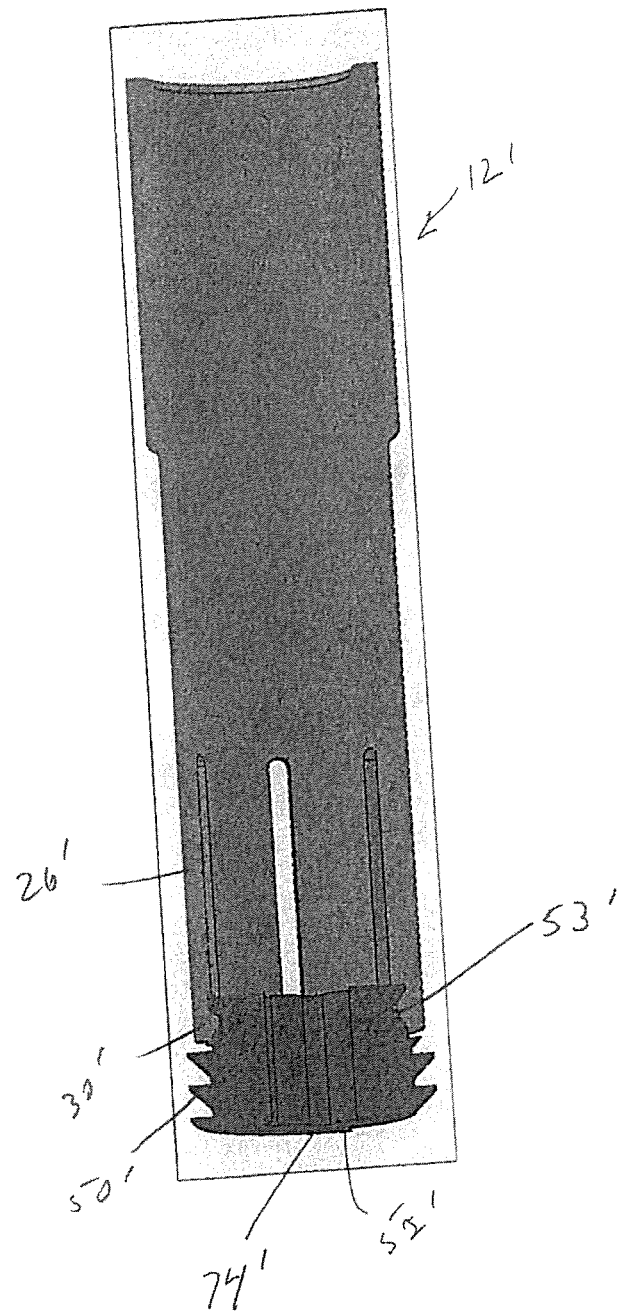
FIG. 18 is a sectional view of the releasably connected drive tool and driven member of FIG. 17 showing locking end portions of resilient arm members of the drive tool releasably secured in an external groove of the threaded driven member.

In addition, one skilled in the art will appreciate variations in the above-described releasable locking arrangement between the tool 12 and locking cap member 22 can be provided. For instance referencing FIGS. 17 and 18, driver tool 12' can be provided to have resilient arm members 26' with slots 34' therebetween and a drive head portion (not shown) similar to corresponding resilient arm members 26 and drive head portion 28 of the driver tool 12. The primary difference is that the resilient arm members 26' have distal locking portion 30' that taken together from a radially enlarged lower flange portion similar to previously described flange portion 31; however, the wedge-shaped locking portions 30' project radially inward from the bottom of the arm members 26' so that the flange portion formed thereby is enlarged in a radial inward direction rather than radial outward direction. In addition, the locking cap member 22' shown in the form of a threaded nut also has external threads 50' and through bore 52'. However, the nut 22' has an upper annular groove 53' formed in its outer surface above the threads 50'.

The locking portions 30' and groove 53' have cooperating surfaces to provide a snap-fit therebetween with the surfaces of locking portions 30' configured similar to surfaces 60-64 of the locking portions 30 and the groove 53' having surfaces similar to at least surfaces 54a and 68 of the undercut pocket 73 of bore portion 54. Thus, the cooperating surfaces include inclined cam surfaces that cause the resilient arm members 26' to resiliently deflect radially outward as the locking nut 22' is being connected thereto with the arm members 26' snapping back radially inwardly so that the locking portions 30' thereof are received in the groove 53'. To separate the tool 12' and the locking nut 22', the reverse operation is employed to cam the locking portions 30' out of the groove 53'. Since the locking cap member or nut 22' has the external groove 30', the through bore 52' need not be provided with differently configured upper and lower portions thereof similar to upper and lower portions 54 and 56 of through bore 52. Instead, the entire through bore 52' can be matched to the lower drive head portion such as by having lobe recesses 74' extending for the full axial extent thereof with the lobed drive head portion provided with an axial length similar to that of the through bore 52'.

Those skilled in the art will recognize that a wide variety of modifications, alterations, and combinations can be made with respect to the above described embodiments without departing from the spirit and scope of the invention, and that such modifications, alterations, and combinations, are to be viewed as being within the scope of the invention.

What is claimed is:

1. A tool for holding or driving an implant member, the tool comprising:
a unitary elongate tool shaft having proximal and distal ends;
a head portion at the distal end of the unitary tool shaft integral therewith so that the tool shaft cannot rotate relative to the head portion and being configured to fit in a recess of the implant member; and
a securing mechanism of the unitary tool shaft integral therewith so that the tool shaft cannot rotate relative to the securing mechanism and being configured to cooperate with the implant member to keep the head portion in the recess with the securing mechanism having a distal end that is disposed at a fixed distance up along the tool shaft toward the proximal end thereof from the distal head portion.

2. The tool of claim 1 wherein the distal head portion has a smaller radial size than the securing mechanism.

3. The tool of claim 1 wherein the securing mechanism comprises a plurality of resilient leg members.

4. The tool of claim 3 wherein the resilient leg members have distal end locking portions, and the head portion projects beyond the distal end locking portions with the locking portions being operable to be releasably locked to the implant member structure with the head portion inserted into the recess.

5. The tool of claim 3 wherein the resilient leg members include slots therebetween, and a radially enlarged lower flange portion having a generally annular configuration interrupted by the slots with the lower flange portion being operable to be releasably locked to the implant member with the head portion inserted into the recess.

6. The tool of claim 5 wherein the radially enlarged lower flange portion projects either radially inward or outward.

7. The tool of claim 1 wherein the head portion is a drive head portion that has a lobed, hexagonal configuration, and the securing mechanism comprises resilient locking portions sized so that diametrically opposite locking portions have an effective diameter thereacross that is larger than a largest effective diameter across diametrically opposite lobes of the drive head portion.

8. The tool of claim 7 wherein the effective diameter across the locking portions is approximately fifty percent larger than the largest effective diameter of the drive head portion.

9. The tool of claim 1 in combination with the implant member wherein the implant member is one of a locking cap member for a pedicle screw assembly and a bone screw for a bone plate.

10. The tool of claim 1 wherein the unitary elongate tool shaft has another head portion at the proximal end identically configured to the head portion at the distal end, and another securing mechanism identically configured to the securing mechanism having the distal end at the fixed distance from the head portion at the distal end of the shaft and having a proximal end that is at the same fixed distance from the head portion at the proximal end to allow for two identical implant members to be secured to the tool shaft.

11. A drive system including a drive tool and a driven member, the drive system comprising:
an elongate shaft of the drive tool having proximal and distal ends and a longitudinal axis extending therebetween;
a drive head portion at the distal end of the elongate shaft and having a radial size thereacross in a radial direction transverse to the shaft longitudinal axis;
a generally annular, resilient flange portion disposed along the elongate shaft such that the drive head portion projects distally beyond the flange portion with the flange portion being radially larger than the radial size of the drive head portion, wherein the generally annular, resilient flange portion comprises a plurality of locking portions spaced circumferentially about the elongate shaft and proximally from the distal end thereof;

a drive portion of the driven member configured for receiving the drive head portion in driving relation therewith; and a generally annular securing portion of the driven member configured for receiving the resilient flange portion via a snap-fit connection therebetween so that advancing the shaft resilient flange portion into engagement with the driven member causes the shaft resilient flange portion to resiliently deflect in the radial direction for releasably locking the driven member to the drive tool by the snap-fit connection.

12. The drive system of claim 11 wherein the elongate shaft includes a plurality of resilient arm members each having a free end, and axial slots between the arm members with the generally annular flange portion comprising the locking portions formed at the free ends of the arm members interrupted by the slots therebetween, the annular securing portion having annular surfaces configured to cooperate with the annular flange portion so that the flange portion is snap-fit to the annular securing portion.

13. The drive system of claim 12 wherein the locking portions at the free ends of the resilient arm members extend radially outward, and the driven member includes a through bore with the generally annular securing portion being a radially enlarged upper portion of the through bore configured for receiving the locking portions snap-fit therein, and the driven member drive portion being a lower drive recess portion of the through bore into which the drive head portion is received in a mating fit therein.

14. The drive system of claim 12 wherein the locking portions at the free ends of the resilient arm members extend radially inward, and the driven member has external threads with the driven member drive portion being a through bore configured for receiving the drive head portion in a mating fit therein, and the generally annular securing portion being an upper annular groove above the external threads configured for receiving the locking portions snap-fit therein.

15. The drive system of claim 12 wherein the locking portions at the free ends of the arm members each have a circumferential spacing from an adjacent one of the locking portions, and the axial slots each have an axial length that is greater than the circumferential spacing between the locking portions at the free ends of the arms.

16. The drive system of claim 11 wherein the flange portion comprising the locking portions and the securing portion have cooperating cam surfaces for releasably locking the driven member to the drive tool by snap-fit connection therebetween with the cam surfaces being configured to require the same pressure to connect and disconnect the drive tool and the driven member.

17. The drive system of claim 11 wherein the driven member is a unitary component such that the drive portion and the generally annular securing portion thereof are integral with each other so that upon rotation of the drive portion, the generally annular securing portion will rotate therewith by the same amount as the drive portion.

* * * * *